US010143381B2

(12) United States Patent
Abe

(10) Patent No.: US 10,143,381 B2
(45) Date of Patent: Dec. 4, 2018

(54) OBJECT INFORMATION ACQUIRING APPARATUS AND CONTROL METHOD THEREFOR

(71) Applicant: CANON KABUSHIKI KAISHA, Tokyo (JP)

(72) Inventor: Hiroshi Abe, Kyoto (JP)

(73) Assignee: CANON KABUSHIKI KAISHA, Tokyo (JP)

(*) Notice: Subject to any disclaimer, the term of this patent is extended or adjusted under 35 U.S.C. 154(b) by 79 days.

(21) Appl. No.: 14/247,332

(22) Filed: Apr. 8, 2014

(65) Prior Publication Data
US 2014/0316244 A1 Oct. 23, 2014

(30) Foreign Application Priority Data

Apr. 19, 2013 (JP) .................. 2013-088195

(51) Int. Cl.
A61B 5/05 (2006.01)
A61B 5/00 (2006.01)
A61B 8/08 (2006.01)
A61B 8/00 (2006.01)
A61B 5/113 (2006.01)

(52) U.S. Cl.
CPC ............ *A61B 5/0095* (2013.01); *A61B 5/489* (2013.01); *A61B 5/7207* (2013.01); *A61B 8/08* (2013.01); *A61B 8/4416* (2013.01); *A61B 5/0035* (2013.01); *A61B 5/113* (2013.01)

(58) Field of Classification Search
CPC ................... A61B 5/04005; A61B 5/04008
See application file for complete search history.

(56) References Cited

U.S. PATENT DOCUMENTS

| 2007/0016050 A1* | 1/2007 | Moehring ............... A61B 8/06 600/454 |
| 2007/0068253 A1* | 3/2007 | Carodiskey ........ G01N 29/0618 73/570 |
| 2010/0049044 A1* | 2/2010 | Burcher ............... A61B 5/0059 600/437 |
| 2011/0178385 A1 | 7/2011 | Fukutani et al. ............. 600/407 |
| 2012/0289833 A1* | 11/2012 | Kashima .................. A61B 8/14 600/445 |
| 2014/0187902 A1 | 7/2014 | Sato et al. ..................... 600/407 |
| 2014/0187936 A1 | 7/2014 | Nakamura et al. ........... 600/437 |

FOREIGN PATENT DOCUMENTS

JP 2010-088497 * 4/2010

* cited by examiner

*Primary Examiner* — Hien Nguyen
(74) *Attorney, Agent, or Firm* — Fitzpatrick, Cella, Harper & Scinto

(57) ABSTRACT

An object information acquiring apparatus is used, which includes: a receiver configured to receive a photoacoustic wave generated from an object irradiated with light and output a time-series electric signal; and a processor configured to acquire characteristic information relating to an inside of the object by using the time-series electric signal, wherein the light is emitted at a plurality of timings, the receiver receives the photoacoustic wave at the plurality of timings, and the processor determines a projection position coordinate on which the time-series electric signal is projected on the basis of an amount of displacement of the inside of the object among the plurality of timings, for each of a plurality of time-series electric signals corresponding to the plurality of timings, and acquires the characteristic information.

15 Claims, 16 Drawing Sheets

PROJECTION DATA REGION 1021

PROJECTION DATA REGION 1022 SUBJECTED
TO DISPLACEMENT AMOUNT CORRECTION

OBJECT INFORMATION ACQUIRING APPARATUS AND CONTROL METHOD THEREFOR

BACKGROUND OF THE INVENTION

Field of the Invention

The present invention relates to an object information acquiring apparatus and a control method therefor.

Description of the Related Art

In optical imaging that irradiates light on an object such as a living body from a light source such as a laser, the inside of the object information obtained on the basis of the incident light have been in progress actively in the medical field. As a kind of this optical imaging technique, there is photoacoustic imaging (PAI). In the photoacoustic imaging, a tissue that absorbs the energy of pulse light and generates elastic waves. The elastic waves propagated in the object and are received. Characteristic information relating to the inside of the object is imaged on the basis of a reception signal of the elastic wave.

When light is irradiated on the object in the photoacoustic imaging, since there is a difference in light absorption coefficient between high absorption area (a tumor of a living body etc.) and the other tissues area, the high absorption area, from the light energy instantaneously expands to generate an elastic wave. Characteristic information is obtained by subjecting a signal obtained by receiving the elastic wave with an acoustic receiver to analysis processing. The characteristic information is optical characteristic value distributions such as an initial sound pressure distribution, a light absorption energy density distribution, and a light absorption coefficient distribution. By measuring these kinds of information by selecting various wavelengths, the information can also be used for quantitative measurement of specific substances (hemoglobin concentration in blood, oxygen saturation in blood, etc.) in the object.

In order to accurately calculate these kinds of characteristic information, it is desired to receive, from the entire circumference, elastic waves three-dimensionally generated in the object and reconstruction an image using reception signals of the elastic waves. However, in most cases, because of physical limitations between the acoustic receiver and a measurement segment, it is difficult to receive the elastic waves from the entire circumference. As a result, since characteristic information is estimated from limited reception conditions, noise such as data omission and a reconstruction artifact occurs in imaged characteristic information. Therefore, in order to avoid this problem, Japanese Patent Application Laid-Open No. 2010-088497 proposes to perform acquisition of photoacoustic waves a plurality of times in different positions, reconstruction an image with respect to reception signals, and acquire characteristic information. The image reconstruction means processing for allocating (projecting) an arbitrarily extracted reception signal (or a projection signal obtained by arbitrarily subjecting the reception signals to processing such as weighting) to reconstruction pixels (voxels).

SUMMARY OF THE INVENTION

The present invention provides an object information acquiring apparatus comprising:
a light source;
a receiver configured to receive a photoacoustic wave generated from an object according to irradiation of light emitted from the light source and convert the photoacoustic wave into a time-series electric signal; and
a processor configured to acquire characteristic information relating to an inside of the object by using the time-series electric signal, wherein
the light source emits light at a plurality of timings,
the receiver receives the photoacoustic wave at the plurality of timings, and
the processor determines a projection position coordinate on which the time-series electric signal is projected on the basis of an amount of displacement of the inside of the object among the plurality of timings, for each of a plurality of time-series electric signals corresponding to the plurality of timings, and acquires the characteristic information by projecting the plurality of time-series electric signals on the determined projection position coordinate.

Further features of the present invention will become apparent from the following description of exemplary embodiments with reference to the attached drawings.

DESCRIPTION OF THE EMBODIMENTS

Figure 1:
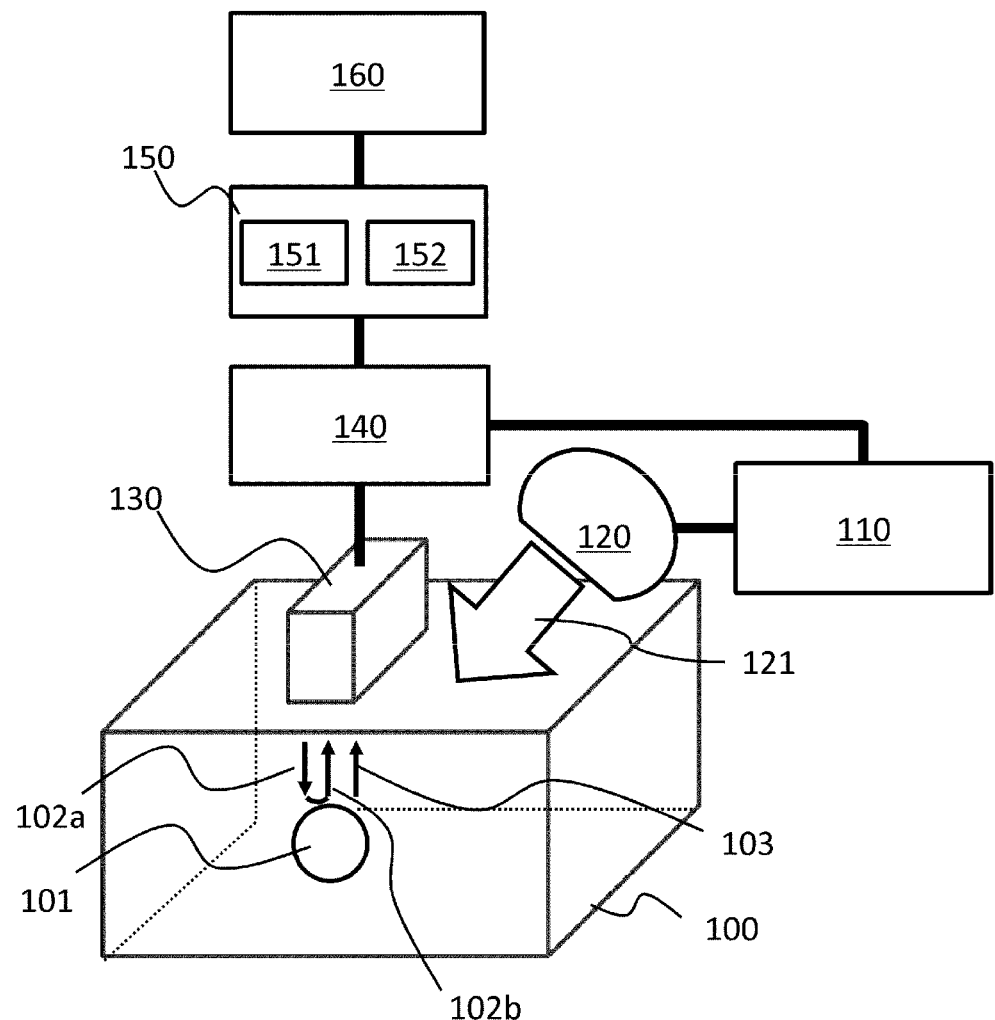
FIG. 1 is a schematic diagram of an object information acquiring apparatus according to the present invention.

Preferred embodiments of the present invention are explained below with reference to the drawings. However, the dimensions, the materials, the shapes, a relative arrangement, and the like of components described below should be changed as appropriate according to the configuration and various conditions of an apparatus applied with the invention and are not meant to limit the scope of the present invention to the description explained below.

An object information acquiring apparatus of the present invention is an apparatus that makes use of a photoacoustic effect for irradiating light (an electromagnetic wave) of an object to thereby receive an acoustic wave generated and propagated in the object and acquiring characteristic information relating to the inside of the object as image data. The object information acquiring apparatus of the present invention includes a transmission function for an ultrasound wave and a function of receiving a reflected wave (an echo wave) from the inside of the object and can use information obtained from the echo wave to, for example, improve an image.

The characteristic information to be obtained indicates a generation source distribution of the acoustic wave caused by the light irradiation, an initial sound pressure distribution in the object or a light energy absorption density distribution and an absorption coefficient distribution derived from the initial sound pressure distribution, and a concentration distribution of substances forming a tissue. The substances forming the tissue are, for example, blood components such as an oxygen saturation distribution and an oxygenated or reduced hemoglobin concentration distribution or fat, collagen, and moisture. Further, information indicating a distribution of acoustic impedance of the inside of the object obtained by applying known information processing to an electric signal based on the echo wave may be grasped as a kind of the characteristic information.

The acoustic wave referred to in the present invention is typically an ultrasound wave and includes an elastic wave called sound wave or acoustic wave. An acoustic wave generated by the photoacoustic effect is referred to as photoacoustic wave or a opto-acoustic wave. In the following explanation, among acoustic waves, an acoustic wave transmitted to the inside of an object by an acoustic receiver and an acoustic wave reflected in the object after the transmission are described as "ultrasound wave". The latter is sometimes described as "echo wave" as well. Among the acoustic waves, an acoustic wave generated in the object by light irradiation is referred to as "photoacoustic wave". However, these descriptions are for convenience of distinction of the acoustic waves and do not limit wavelengths and the like of the acoustic waves.

In the present invention, it is preferable to sampling a plurality of photoacoustic waves in time-series while changing a direction and a position of the acoustic receiver with respect to the object and reconstruction by using the sampling data obtained in time-series. The change of the direction and the like can be realized by an operator bringing, for example, a handheld probe functioning as the acoustic receiver into contact with the object while swinging the handheld probe. Consequently, the reconstruction is performed with a wider aperture compared with the reconstruction performed using data obtained by performing measurement once (or from only a specific direction). That is, by swinging the acoustic receiver with respect to a region of interest inside the object, three-dimensionally generated acoustic waves are grasped at a larger solid angle. As a result, it is possible to more accurately estimate and reproduce actual characteristic information through the reconstruction performed using time-series reception signals of photoacoustic waves obtained in a plurality of positions.

However, in the method explained above, it is necessary to receive the photoacoustic waves at a plurality of timings while changing the direction and the position of the acoustic receiver with respect to the object. Therefore, when a plurality of times of measurement is actually applied to a biological tissue, the measurement involves movements such as a pulsation and a blood flow. It is likely that displacement occurs inside the object among the respective timings. In this case, if characteristic information is acquired by the reconstruction performed using the time-series reception signals without taking into account the displacement in the inside of the object, it is difficult to accurately estimate and reproduce the characteristic information. Therefore, in the present invention, determination of projection position coordinates on which a plurality of time-series reception signals obtained at the plurality of timings are projected is performed on the basis of an amount of displacement of the inside of the object among the plurality of timings. That is, in the present invention, for each sampling data of the plurality of time-series reception signals obtained at the plurality of timings, determination of projection position coordinates on which the each sampling data is projected is performed on the basis of an amount of displacement of the inside of the object among the plurality of timings.

Consequently, even when displacement occurs inside the object among the plurality of timings, it is possible to accurately estimate and reproduce actual characteristic information on the basis of the projection position coordinates determined in consideration of the displacement occurs inside the object among the plurality of timings.

After the characteristic information is acquired on the basis of the time-series reception signals obtained at the plurality of timings by the image reconstruction, it is difficult to correct an error due to the displacement inside the object among the plurality of timings.

(Apparatus Configuration)

The object information acquiring apparatus according to the present invention is explained with reference to a schematic diagram of FIG. 1. The apparatus includes a light source 110, an optical system 120, an acoustic receiver 130, a control device 140, a signal processing device 150, and a display device 160. The components are explained below.

(Object 100 and Light Absorber 101)

Although an object 100 and a light absorber 101 do not configure a part of the object information acquiring apparatus of the present invention, the object 100 and the light absorber 101 are explained below. Main purposes of the object information acquiring apparatus of the present invention are diagnosis of malignant tumors, vascular diseases, and the like of a person and an animal, follow-up of chemical treatment, and the like. Therefore, as the object 100, a living body, specifically, a target segment of diagnosis such as the breast, the neck, or the abdomen of a human body or an animal is assumed.

The light absorber 101 present inside the object 100 indicates a light absorber having a relatively high absorption coefficient inside the object 100. For example, if a human body is a measurement target, oxyhemoglobin or deoxyhemoglobin, a blood vessel including a large amount of oxyhemoglobin or deoxyhemoglobin, or a malignant tumor including a large number of newborn blood vessels is the light absorber 101. Besides, plaque of the carotid artery wall or the like is the light absorber 101.

(Light Source 110)

As the light source 110, a pulse light source capable of generating pulse light in several nanosecond to several microsecond order is preferable. Specifically, in order to efficiently generate a photoacoustic wave, pulse width of about 10 nanoseconds is used. As the light source 110, a light-emitting diode or the like can be used instead of a laser. As the laser, various lasers such as a solid-state laser, a gas laser, a dye laser, and a semiconductor laser can be used. The wavelength of irradiated light is desirably a wavelength with which light propagates to the inside of the object 100. Specifically, when the object 100 is a living body, the wavelength is equal to or larger than 500 nm and equal to or smaller than 1200 nm.

(Optical System 120)

Light emitted from the light source 110 is guided to the object 100 while being processed into a desired light distribution shape typically by optical components such as a lens and a mirror. It is also possible to propagate the light using, for example, a light guide such as an optical fiber. The optical system 120 includes, for example, a mirror that reflects the light, a lens that condenses or expands the light or changes the shape of the light, and a diffuser that diffuses the light. As such optical components, any optical components may be used as long as the light emitted from the light source 110 is irradiated on the object 100 in a desired shape. The light is more preferably spread to a region of a certain degree than being condensed by the lens from a viewpoint of safety for a living body and expansion of a diagnosis region.

(Acoustic Receiver 130)

The acoustic receiver 130 receives an acoustic wave (a photoacoustic wave and an echo wave) and converts the acoustic wave into an analog electric signal. Any acoustic receiver such as an acoustic receiver that makes use of a piezoelectric phenomenon, resonance of light, a change in capacitance, or the like may be used. The acoustic receiver 130 is preferably an acoustic receiver in which a plurality of transducers that transmit and receive the acoustic wave are arrayed. Consequently, it is possible to receive the acoustic wave in a plurality of positions and output a plurality of signals. Therefore, it is possible to expect a reduction in a measurement time and improvement of an SN ratio.

The acoustic receiver 130 is usually provided in a form of a probe in which a transducer is held in a housing. In this specification, the acoustic receiver is also referred to as probe.

The acoustic receiver 130 is preferably capable of changing the position thereof with respect to the object 100. If the acoustic receiver 130 is a handheld probe, the position is changed by manipulation of an operator. However, a scanning mechanism for the acoustic receiver 130 can also be set. The object information acquiring apparatus can also give a guide instruction for swinging to the operator in a form of sound or screen display.

The acoustic receiver 130 preferably includes a function of a transmitter for transmitting an ultrasound wave to the object 100 and a function of a receiver for receiving an echo wave propagated through the inside of the object 100. Consequently, it is possible to expect signal detection in the same region and space saving. However, the transmitter and the receiver may be separately provided. Receivers for a photoacoustic wave and an echo wave may be separately provided. The acoustic receiver 130 is equivalent to a receiver of the present invention.

(Control Device 140)

The control device 140 applies amplification processing and digital conversion processing to the analog electric signal output from the acoustic receiver 130. The control device 140 typically includes an amplifier, an A/D converter, a field programmable gate array (FPGA) chip, and a CPU. When the acoustic receiver 130 includes a plurality of transducers and outputs a plurality of reception signals, it is desirable that the control device 140 can simultaneously process a plurality of signals. Consequently, it is possible to reduce a processing time.

The control device 140 controls timings of irradiation of pulse light and reception of a photoacoustic wave following the irradiation of the pulse light. Specifically, the control device 140 performs control of irradiation timing of the pulse light and control of transmission and reception timings of an electric signal using the pulse light as a trigger signal.

In the present invention, a photoacoustic wave signal is a concept including the time-series analog electric signal output from the acoustic receiver 130 and the time-series signal processed by the control device 140. An ultrasound wave signal is a concept including the time-series analog electric signal output from the acoustic receiver 130 that receives the echo wave and the time-series signal after the processing in the control device 140.

(Signal Processing Device 150)

The signal processing device 150 generates information concerning the inside of the object 100 on the basis of a digital signal. As the signal processing device 150, an information processing device such as a workstation is typically used. Correction processing, image reconstruction processing, and the like explained below are performed by software programmed in advance.

The software includes a displacement amount calculation module 151 that performs correction processing, which is characteristic processing of the present invention. The software includes an image reconstruction module 152. The modules may be provided as devices separate from the signal processing device 150. The signal processing device 150 can apply signal processing to both of a 2D space and a 3D space.

The displacement amount calculation module 151 calculates an amount of displacement of the acoustic receiver 130, for example, amounts of change of the direction and the position of the handheld probe by the manipulation of the operator. The displacement amount calculation module 151 can also calculate an amount of displacement of the inside of the object 100 due to pressing of the handheld probe, a body motion, and the like.

The image reconstruction module 152 performs image reconstruction using the photoacoustic wave signal and forms characteristic information. The image reconstruction module 152 generates characteristic information such as an acoustic impedance distribution of the object 100 using the ultrasound wave signal.

As an image reconstruction algorithm, a method known in the tomography technique is used. The method is, for example, back projection in a time domain or a Fourier domain, phasing addition (delay and sum), or the like. When a long time can be used for reconstruction, an image reconstruction method such as an inverse problem analysis method by repetition processing may be used.

The image reconstruction module 152 applies delay addition processing for matching phases and addition processing after the delay addition processing to the ultrasound wave signal. Consequently, it is possible to form characteristic information such as acoustic impedance in the object 100 and speckle pattern data due to scattering in the object 100.

In the photoacoustic imaging, by using the focused acoustic receiver 130, it is possible to form a characteristic information image in a living body without image reconstruction. In such a case, signal processing performed using the image reconstruction algorithm is unnecessary.

Each of the displacement amount calculation module 151 and the image reconstruction module 152 typically includes a device such as a CPU or a GPU and a circuit such as an FPGA or an ASIC. Each of the displacement amount calculation module 151 and the image reconstruction module 152 may include a plurality of devices and a plurality of circuits rather than one device and one circuit. Any one of the devices and the circuits may execute respective kinds of processing performed by the displacement amount calculation module 151 and the image reconstruction module 152.

The control device 140 and the signal processing device 150 are sometimes integrated. In this case, characteristic information such as acoustic impedance of the object 100 and an optical characteristic value distribution can be generated by hardware processing rather than software processing performed by the workstation. The control device 140 and the image reconstruction module 152 of the signal processing device 150 are equivalent to a processor of the present invention. The displacement amount calculation module 151 is equivalent to a detector of the present invention.

(Display Device 160)

The display device 160 displays the characteristic information such as the optical characteristic value distribution output from the signal processing device 150. As the display device 160, for example, a liquid crystal display, a plasma display, an organic EL display, and an FED can be used. The display device 160 can be provided separately from a main body of the object information acquiring apparatus. For example, acquired object information may be displayed on the display device 160 by wire or radio. The display device 160 is equivalent to a display unit of the present invention.

(Processing Flow)

Figure 2:
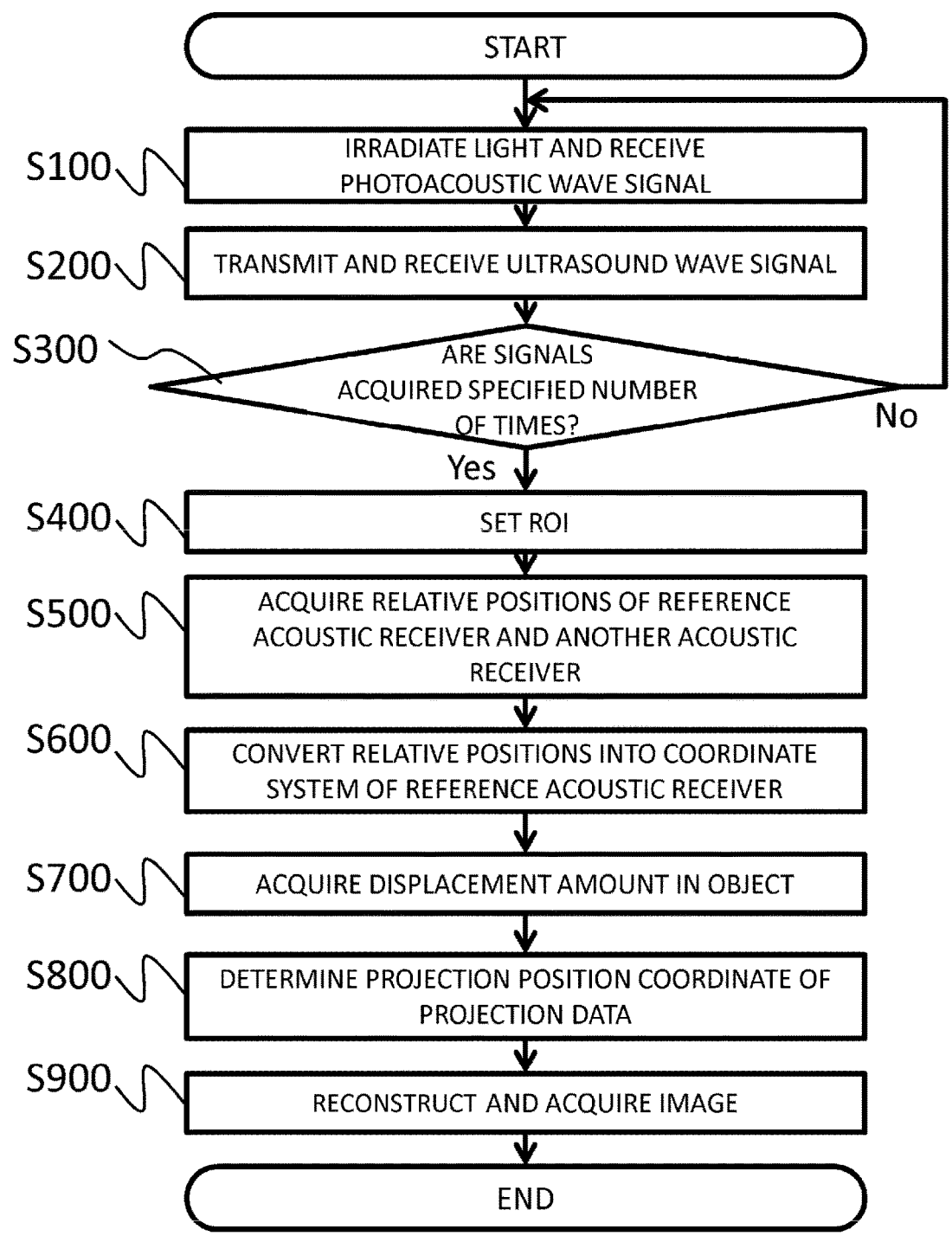
FIG. 2 is a diagram showing a flow of an object information acquiring method according to the present invention.

A procedure of an object information acquiring method performed by controlling the object information acquiring apparatus is explained with reference to a flowchart of FIG. 2.

(S100: Step of Acquiring a Photoacoustic Wave Signal)

In this step, the acoustic receiver 130 receives a photoacoustic wave generated from the object 100 and generates a photoacoustic wave signal.

First, pulse light 121 emitted from the light source 110 is irradiated on the object 100 via the optical system 120. The pulse light 121 is absorbed by the light absorber 101 and a photoacoustic wave 103 is generated. The control device 140 detects the emission of the pulse light 121 and causes the acoustic receiver 130 to start reception of the photoacoustic wave 103. The photoacoustic wave signal output from the acoustic receiver 130 is stored on a memory through processing in the control device 140.

In this embodiment, this step is performed at a plurality of timings.

(S200: Step of Acquiring an Ultrasound Wave Signal)

In this step, an ultrasound wave is transmitted to and received from the object 100, whereby characteristic information such as acoustic impedance of the object 100 and data such as a speckle pattern due to scattering in the object 100 are acquired. The acoustic impedance can be used for, for example, displacement amount calculation by the acoustic receiver 130 in S500. The speckle pattern can be used for, for example, calculation of an amount of displacement of the inside of the object 100 due to, for example, pressing of the handheld probe.

The acoustic receiver 130 transmits an ultrasound wave 102*a* to the object 100. The transmitted ultrasound wave is reflected in the object 100 and changes to an echo wave 102*b*. The acoustic receiver 130 receives the echo wave 102*b* and outputs an ultrasound wave signal. The control device 140 stores the ultrasound wave signal on the memory after performing amplification and A/D conversion processing.

Timing for transmitting the ultrasound wave 102*a* may be simultaneous with the pulse light 121 in S100. The number of times of transmission and reception of the ultrasound wave is not limited to one. The transmission and reception may be performed a plurality of times before the next pulse light irradiation.

(S300: Step of Determining the Number of Times of Repetition of S100 and S200)

In this step, the signal processing device 150 determines whether the number of times of acquisition of the photoacoustic wave signal in S100 and the number of times of acquisition of the ultrasound wave signal in S200 reach a predetermined number. If the numbers of times of acquisition do not reach the predetermined number, S100 and S200 are repeated.

As the number of times of repetition, a desired number of times is set in advance. Alternatively, before starting measurement, the operator may input the number of times of repetition from input means such as a touch panel or a keyboard. Alternatively, it may be possible to enable determination of the number of times while performing measurement, for example, set the measurement to be repeated while a push button set on the outside is depressed. As an example of the setting for determining the number of times while performing the measurement, it is also possible to provide a contact sensor in the handheld probe and allow the measurement to be performed while the operator places the handheld probe on the object 100.

(S400: Step of Setting a Region of Interest of a Photoacoustic Wave)

In this step, the image reconstruction module 152 sets a region of interest (ROI). In this flow, the ROI indicates a region where reconstruction is performed on the basis of the photoacoustic wave signal (a region where an optical characteristic value distribution is calculated).

When the ROI is set, an image region of any one ultrasound wave image among ultrasound wave images reconstruction from ultrasound wave signals repeatedly measured in S200 only has to be used. For example, among a plurality of ultrasound wave images, a first measured image, a last measured image, a measured image in the number of times in the middle, and the like are used. The measured images may be displayed on the display device 160. The operator may arbitrarily set the ROI. In this case, an input device such as a mouse or a touch panel and an input method for indicating a coordinate can be used.

(S500: Step of Acquiring Positions of the Acoustic Receiver and the ROI at the Time of Photoacoustic Wave Reception)

In this step, the displacement amount calculation module 151 functioning as a second detector calculates an amount of displacement between a position of the acoustic receiver 130 at the time when the ultrasound wave image in which the ROI is set in S400 is acquired and a position of the acoustic receiver 130 at the time when the photoacoustic wave is received in step S100. The amount of displacement is represented by translation (movement amounts in a direction (X) along the acoustic receiver 130 and a lower surface direction (Y) perpendicular to the acoustic receiver 130), a rotation value ($\theta$), and the like. Such displacement is caused by the operator moving the handheld probe with manipulation or mechanically three-dimensionally scanning a three-dimensionally arranged probe.

In the displacement amount calculation, there is a method of arranging a magnetic sensor in the acoustic receiver 130 and calculating an amount of displacement from fluctuation in magnetism. There is also a method of arranging an optical sensor such as an optical trackball in the acoustic receiver 130 and measuring an infrared ray used for the optical sensor. When the acoustic receiver 130 is controlled by a stepping motor or the like along a predetermined shape, the amount of displacement may be calculated using control data.

The amount of displacement can also be calculated using the ultrasound wave signal acquired in S200 or an ultrasound wave image based on the ultrasound wave signal. This method is preferable in that an external sensor and machinery are not used. The ultrasound wave image has characteristics due to the acoustic impedance and the speckle pattern. A correlation among images can be calculated on the basis of the acoustic impedance and the speckle pattern.

In this case, the displacement amount calculation module 151 applies a known algorithm such as block matching method to the ultrasound wave images. In the block matching method, an image is divided into image regions (blocks) of a fixed size, positions of blocks corresponding to the images in the ultrasound wave images are searched, and movement and rotation amounts of the blocks are calculated. As an evaluation function for a region to be searched, known indexes S indicating the correlation values of the images are used. A motion vector in which correlation is calculated highest in a search range is calculated as an amount of displacement of the blocks.

As the indexes S of the correlation values, there are a sum of absolute difference (SAD), a sum of squared difference (SSD), a cross-correlation (CC), and the like. As the index S, there are also a normalized cross-correlation (NCC), a zero-mean normalized cross-correlation (ZNCC), and the like. These indexes S may be complemented and corrected by values of the blocks near the indexes S.

For example, concerning the SAD, when pixels in blocks of both images are represented as f(i, j) and g(i, j), the index S is indicated by the following Expression (1):

[Math. 1]

$$S_{SAD} = \sum_i \sum_j |f(i, j) - g(i, j)|. \quad (1)$$

Concerning the SSD, the index S is indicated by the following Expression (2):

[Math. 2]

$$S_{SSD} = \sum_i \sum_j \{f(i, j) - g(i, j)\}^2. \quad (2)$$

Concerning the CC, the index S is indicated by the following Expression (3):

[Math. 3]

$$S_{CC} = \sum_i \sum_j f(i, j) g(i, j). \quad (3)$$

Concerning the NCC, the index S is indicated by the following Expression (4):

[Math. 4]

$$S_{NCC} = \frac{\sum_i \sum_j f(i, j) g(i, j)}{\sqrt{\sum_i \sum_j f(i, j)^2 \times \sum_i \sum_j g(i, j)^2}}. \quad (4)$$

Concerning the ZNCC, the index S is indicated by the following Expression (5):

[Math. 5]

$$S_{ZNCC} = \frac{\sum_i \sum_j ((f(i, j) - \bar{f})(g(i, j) - \bar{g}))}{\sqrt{\sum_i \sum_j f(i, j - \bar{f})^2 \times \sum_i \sum_j g(i, j - \bar{g})^2}}. \quad (5)$$

When a correlation value of the image regions is calculated, the index S of a highest correlation value among correlation values calculated by the displacement amount calculation module 151 is extracted. As a method for region division, there is a method of dividing an image region into rectangles or the like having an equal area. When the image region is divided, a division range and the number of divisions may be changed according to a brightness value or the like of an image.

There are various methods for the displacement amount calculation by the acoustic receiver 130 in the block matching method. It is also possible to perform the search targeting only a rectangular region near the acoustic receiver 130 and directly set a difference between a found rectangular region and the original rectangular region as an amount of displacement. It is also possible to calculate the amounts of displacement of rectangular regions around the acoustic receiver 130, perform an approximation operation by linear interpolation using the displacement amounts, and calculate an amount of displacement of the acoustic receiver 130 itself. Alternatively, an average of displacement amounts of a large number of rectangular regions may be used. When displacement cannot be accurately calculated at a screen end or the like, an error may be reduced using a mode.

When the position of the acoustic receiver 130 is calculated from the ultrasound wave image, a position at the point of ultrasound wave signal reception is calculated. When such position information is used for correction of a photoacoustic image, it is necessary to associate timing of ultrasound wave signal reception and timing of photoacoustic wave signal reception.

As an example of such association, the position of the acoustic receiver 130 at the time of ultrasound wave signal reception may be approximately set as the position of the acoustic receiver 130 at the time of photoacoustic wave reception. Further, the position of the acoustic receiver 130 at the time of photoacoustic wave reception may be estimated from the position of the acoustic receiver 130 at the time of ultrasound wave reception performed before and after the photoacoustic wave reception.

(S600: Step of Rotating and Moving the Photoacoustic Wave Signal on the Basis of the Displacement Amount of the Acoustic Receiver)

In this step, the image reconstruction module 152 converts a coordinate system of the acoustic receiver 130 at the time of photoacoustic wave signal reception on the basis of the displacement amount of the acoustic receiver 130 calculated in S500. Consequently, it is possible to compare and combine photoacoustic signals deriving from photoacoustic waves acquired from different directions after aligning the photoacoustic signals according to the same reference.

For example, the displacement angle calculated in S500 is represented as θ, a horizontal direction movement amount is represented as x', and a movement amount in a direction perpendicular to the horizontal direction is represented as y'. Then, concerning position vectors x0 and y0 of the acoustic receiver 130, position vectors x1 and y1 of the acoustic receiver 130 after coordinate conversion are represented by the following Expression (6):

[Math. 6]

$$\begin{pmatrix} x_1 \\ y_1 \end{pmatrix} = \begin{pmatrix} \cos\theta & -\sin\theta & x' \\ \sin\theta & \cos\theta & y' \end{pmatrix} \begin{pmatrix} x_0 \\ y_0 \\ 1 \end{pmatrix}. \quad (6)$$

Figure 9:
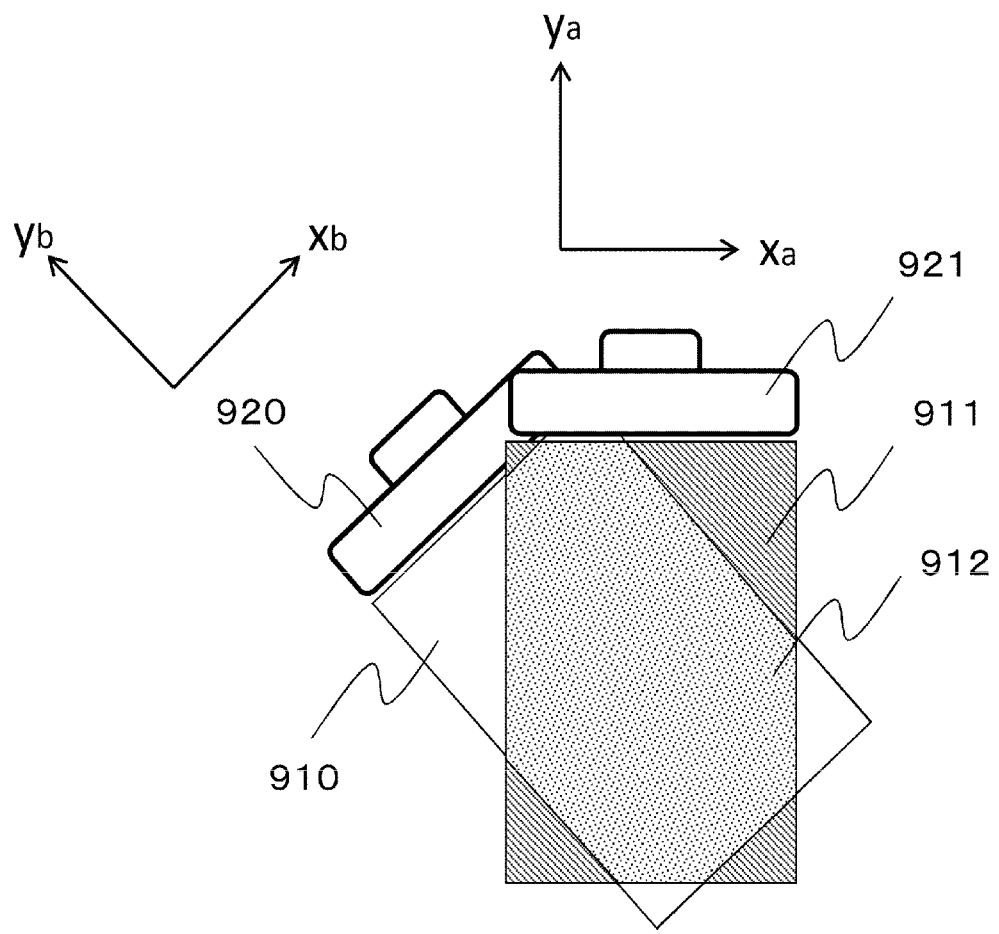
FIG. 9 is a diagram showing a memory storage region of the object information acquiring apparatus according to the fourth embodiment.

This coordinate conversion is executed respectively on the basis of displacement amounts and coordinate systems are stored on the memory inside the signal processing device 150. An example of coordinate systems corresponding to the positions and the directions of the acoustic receiver 130 is shown in FIG. 9. In this example, a signal acquired by an acoustic receiver 921 when a displacement amount is measured in a vertical lower direction is represented by an $x_a$-$y_a$ coordinate system. A signal acquired by an acoustic receiver 920 when a displacement amount is measured obliquely is represented by an $x_b$-$y_b$ coordinate system.

When the displacement amount of the acoustic receiver 130 is very small from a result in S500 and it is unnecessary to correct an error of the displacement amount, S600 may be omitted.

(S700: Step of Acquiring a Displacement Amount in the Object)

In this step, the displacement amount calculation module 151 functioning as the first detector calculates an amount of displacement in the object 100 between different images using the object information acquired in S200 or S100.

The calculation of a amount of displacement in the object 100 is performed by comparing image regions in the object 100. First, the image reconstruction module 152 performs image reconstruction of the object 100 on the basis of the coordinate systems aligned in step S600. Subsequently, the displacement amount calculation module 151 calculates displacement amounts concerning the image regions according to an algorithm and stores the displacement amounts on the memory inside the signal processing device 150. As an example of the algorithm, a speckle tracking method for calculating a displacement amount using a speckle pattern known in the field of ultrasound wave images can be used.

The displacement amounts of the image regions only have to be calculated for each of the image regions divided in a lattice shape. More preferably, the displacement amounts are calculated in a lattice size adjusted to a pitch of pixels desired to be reconstruction in the ROI.

(S800: Step of Determining a Projection Position Coordinate on the Basis of the Displacement Amount in the Object)

In this step, the image reconstruction module 152 determines a projection position coordinate of the photoacoustic wave signal data on the basis of the displacement amount in the object 100 calculated in S700. When a space to be projected is three-dimensional, the projection position coordinate is referred to as projection position voxel. When the space to be projected is two-dimensional, the projection position coordinate is referred to as projection position pixel.

The photoacoustic wave signal data indicates data for allocating photoacoustic signal to the projection position voxel according to time series when reconstruction is performed in a time domain. Besides, the photoacoustic wave signal data may be any signal as long as the photoacoustic wave signal data is based on photoacoustic signal received by the transducers in time series. For example, the photoacoustic wave signal data may be the photoacoustic wave signal (an RF signal) acquired in S100, an RF signal subjected to envelope detection, a signal obtained by applying fixed weighting to the RF signal, or a signal obtained by convoluting a certain coefficient in the RF signal. Besides, the photoacoustic wave signal data may be, for example, a signal obtained by subjecting the RF signal to weighting corresponding to an angle between a normal vector of the acoustic receiver 130 and a vector between the acoustic receiver 130 and the projection position voxel.

The projection data is explained with reference to FIGS. 10A to 10D.

Figure 10A:
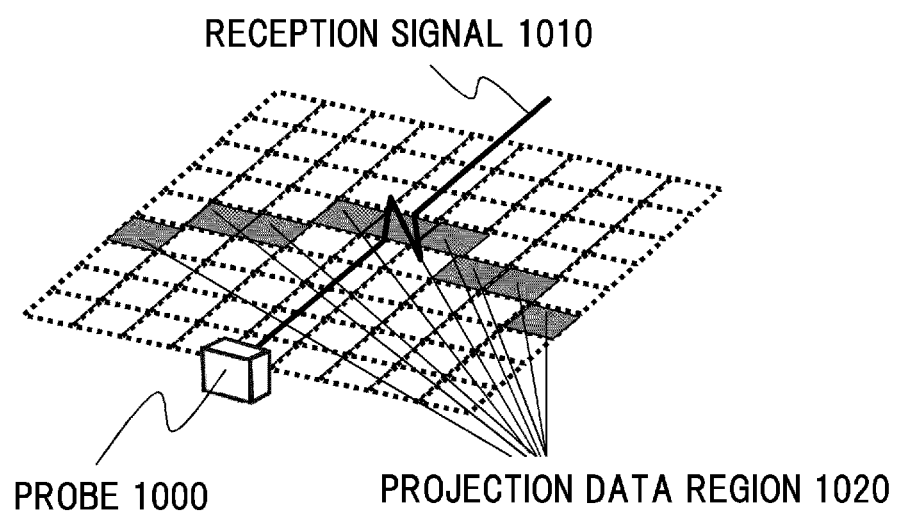
FIG. 10A is a diagram for explaining a relation between an acoustic receiver and a region where a signal is received.
Figure 10B:
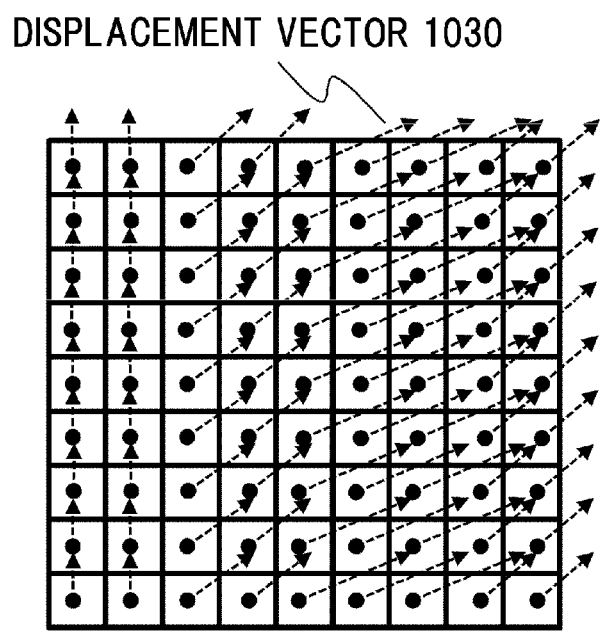
FIG. 10B is another diagram for explaining the relation between the acoustic receiver and the region where a signal is received.
Figure 10C:
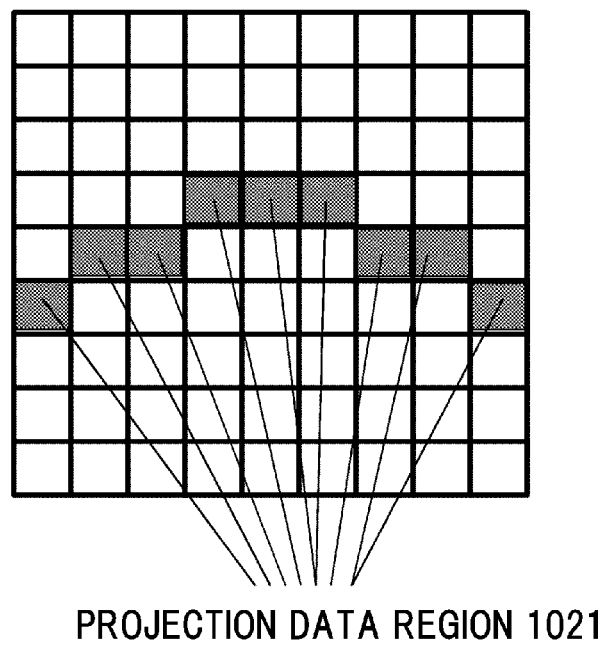
FIG. 10C is another diagram for explaining the relation between the acoustic receiver and the region where a signal is received.
Figure 10D:
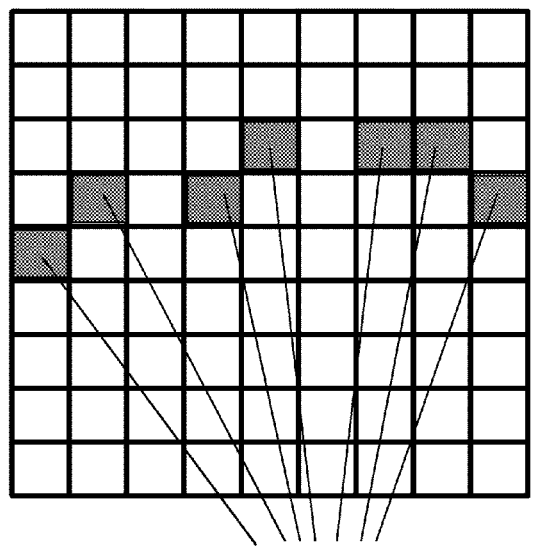
FIG. 10D is another diagram for explaining the relation between the acoustic receiver and the region where a signal is received.

In FIG. 10A, one transducer of an acoustic receiver 1000 and image regions obtained by dividing the inside of the object 100 in a lattice shape are shown. When the acoustic receiver 1000 receives a photoacoustic signal 1010, it is estimated from time from light irradiation and sound speed in the object 100 that a sound source is present in any one of image regions (referred to as projection data regions 1020) of concentric circle shapes present at equal distance from the acoustic receiver 1000. As shown in FIG. 10B, the displacement amount data calculated in S700 is represented by displacement vectors 1030 in divided regions. As shown in FIG. 10C, correction performed using the displacement vectors 1030 is applied to regions divided in the same size as the size shown in FIG. 10B. Then, projection data regions 1021 in FIG. 10C move according to the vectors and change to projection data regions 1022 formed taking into account displacement amounts in FIG. 10D.

For example, in a universal back projection (UBP) method, an initial sound pressure distribution $p_0(r)$ is estimated on a time space by the following Expression (7):

[Math. 7]

$$p_0(r) = \int_{\Omega_0} b(r_0, t = |r - r_0|) \frac{d\Omega_0}{\Omega_0}. \quad (7)$$

A term $b(r_0, t)$ equivalent to the projection data at this point is indicated by the following Expression (8):

[Math. 8]

$$b(r_0, t) = p(r_0, t) - 2t \frac{\partial p(r_0, t)}{\partial t}. \quad (8)$$

A term $d\Omega_0$ of the acoustic receiver 130 with respect to an arbitrary data region is represented by the following Expression (9):

[Math. 9]

$$d\Omega_0 = \frac{dS_0}{|r-r_0|^2}\cos\theta. \qquad (9)$$

In the expression, p(r) represents the photoacoustic signal acquired in S100, r represents a position, t represents time, and θ represents an angle formed by the acoustic receiver 130 and an arbitrary data region.

When the distance between a sound source and a measurement position is sufficiently large compared with the size of the sound source, the projection data term $b(r_0, t)$ may be set as represented by the following Expression (10):

[Math. 10]

$$b(r_0, t) = -2t\frac{\partial p(r_0, t)}{\partial t}. \qquad (10)$$

At this point, t of the projection data changes according to the position of the projection position voxel determined in S700. Therefore, the projection data term $b(r_0, t)$ is extracted using t with respect to the projection position voxel determined in this step.

For example, in the delay and sum (DAS) method or the phasing addition method, the initial sound pressure distribution $p_0(r)$ is estimated on a time space by the following Expression (11):

[Math. 11]

$$p_0(r) = \frac{1}{M}\sum_{i=1}^{M}\omega * S_i(t+\tau). \qquad (11)$$

In the expression, τ represents a delay time from M transducers to projection position voxels calculated from an x coordinate $x_f$, a y coordinate $y_f$, sound velocity $c_0$ of an f-th projection position voxel from an i-th transducer represented by the following Expression (12):

[Math. 12]

$$\tau=\sqrt{(x_f^2+y_f^2)/c_0} \qquad (12)$$

In Expression (11), ω represents a weight factor such as a window function and is changed according to directivity of the transducers and desired resolution and SN of a reconstruction image.

As projection data in consideration of displacement in object, sampling data Si obtained by aligning phases of signals received by the transducers with the projection position voxels is extracted.

When a displacement amount of the inside of the object 100 is very small from a result of S700 and it is unnecessary to correct an error of the displacement amount, S800 may be omitted.

Instead of correcting the projection position coordinate in this process, a coordinate system of projection data at timings may be corrected on the basis of displacement amounts of the inside of the object 100 at the timings as in S600.

Instead of correcting the coordinate system of the photoacoustic signal in S600, a projection position coordinate in which the photoacoustic signal is projected may be corrected on the basis of the displacement amount of the acoustic receiver 130 as in the step of the process.

(S900: Step of Performing Projection Data Image Reconstruction Determined on the Basis of a Displacement Amount of the Inside of the Object)

In this step, the image reconstruction module 152 performs image reconstruction of the ROI from projection data signals of all frames based on the projection data extracted in S800 according to, for example, Expression (7) in the UBP or Expression (11) in the DAS. Alternatively, when a displacement amount of the inside of the object 100 is not taken into account, the image reconstruction is performed from the original photoacoustic wave signal.

The display device 160 displays a photoacoustic wave image and an ultrasound wave image subjected to the image reconstruction as images. The images may be superimposed or translated to be displayed as a single image or the images may be switched and displayed.

First Embodiment

In this embodiment, a method of acquiring a corrected photoacoustic image from a photoacoustic signal deriving from photoacoustic waves received a specified number of times and an ultrasound wave signal deriving from an echo wave is explained. A flow itself of processing is the same as the flow shown in FIG. 2. The number of times of signal acquisition in step S300 is set to 100.

A 1D linear array probe is used as the acoustic receiver 130. As an apparatus configuration, an instruction concerning probe scanning is displayed on a screen while the probe is scanned to acquire data. A message of data acquisition completion is displayed after the end of a predetermined sequence. As an operation instruction to an operator, an instruction for moving the probe to measure an object from a plurality of directions is preferable.

After a sequence is started, first, a photoacoustic wave signal is acquired in S100. Subsequently, an ultrasound wave signal is acquire in S200.

Figure 3:
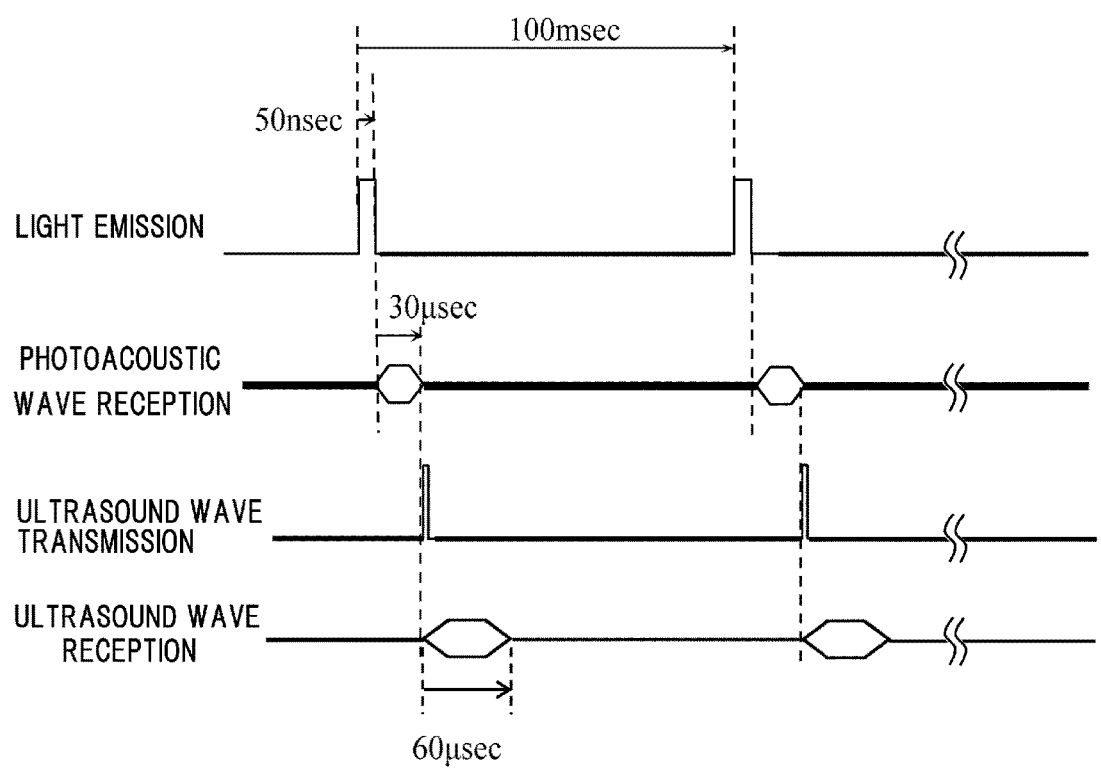
FIG. 3 is a diagram for explaining a time chart of an object information acquiring apparatus according to a first embodiment.

Timings of S100 and S200 are explained with reference to a timing chart of FIG. 3. A photoacoustic wave signal is acquired for a predetermined time (e.g., 300 μsec) by being triggered by light emission. An interval of the light emission is determined from a light emission frequency of the light source 110. For example, when the light emission frequency is 10 Hz, the interval of the light emission is 100 msec. When a light emission time of one light emission is 50 nsec, time from the end of the acquisition of the photoacoustic signal to the next light emission is equal to or longer than 99 msec. Transmission of an ultrasound wave is performed in that period. After the transmission, an echo wave is acquired for a predetermined time (e.g., 60 μsec).

Figure 4:
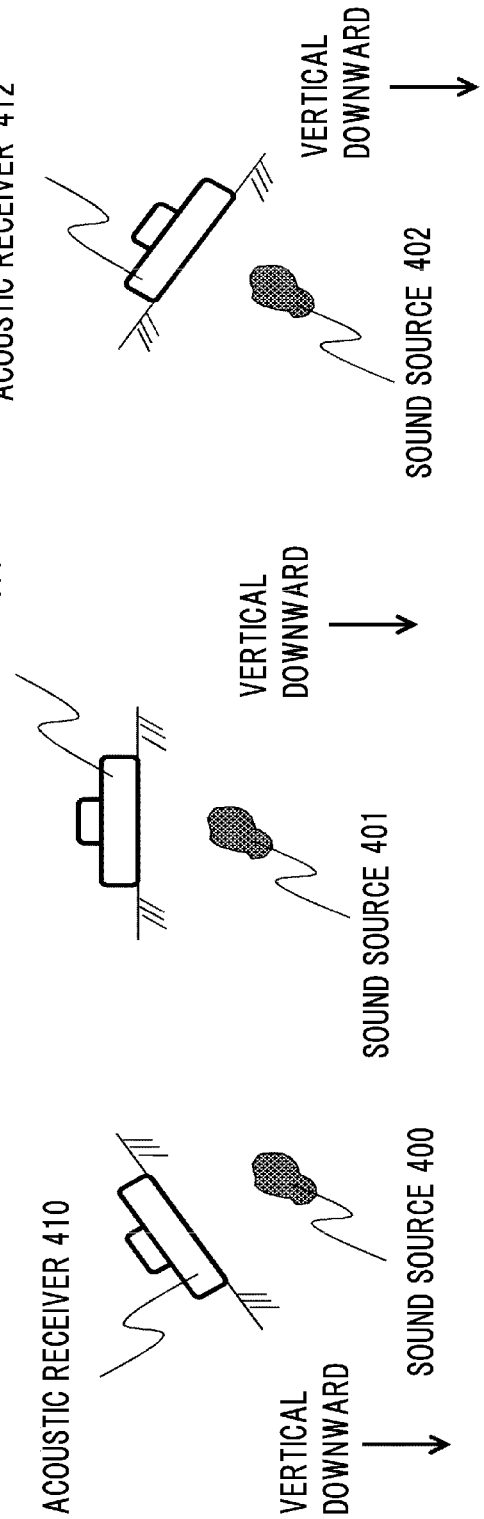
FIGS. 4A to 4C are diagrams showing an operation range of an acoustic receiver according to the first embodiment.

In this embodiment, while the step is repeated one hundred times in S300, an acoustic receiver is varied as shown in FIGS. 4A to 4C. First, as shown in FIG. 4A, an acoustic receiver 410 is arranged such that the normal of a receiving surface of the acoustic receiver 410 is about 20 degrees obliquely to the vertical downward direction. The acoustic receiver 410 acquires a photoacoustic wave and an echo wave from a sound source 400 in the object. The acoustic receiver 410 is gradually moved to change the angle. In FIG.

4B in the middle, an acoustic receiver 411 receives a photoacoustic wave signal from a sound source 401 present in the vertical downward direction. In FIG. 4C, an acoustic receiver 412 is arranged in the opposite direction of FIG. 4A. The acoustic receiver 412 receives a signal from a sound source 402 in a direction tilting about 20 degrees with respect to the vertical downward direction. In FIGS. 4A to 4C, signals are received in respective positions and information is stored according to coordinate systems in the positions.

Concerning the setting of the ROI in S400, a region having width of 40 mm and depth of 30 mm corresponding to an acoustic receiver size is extracted from a reconstruction image based on an ultrasound wave signal measured for the fiftieth time.

Concerning the displacement amount calculation for the probe in S500, an image obtained by reconstruction ultrasound wave signals for one hundred times with the image reconstruction module 152 is divided. Movements of divided regions are tracked. Specifically, first, a region having width of 30 mm and depth of 10 mm right under the probe is divided into a 2-mm square regions. Subsequently, concerning the divided regions, translation amounts and rotation amounts having highest correlation are calculated using ZNCC as a correlation index with reference to the fiftieth image used for the ROI setting. A mode among the values is set as a displacement amount of the probe.

Concerning the coordinate system conversion in S600, coordinate systems of the acoustic receiver at the time of acquisition of ultrasound waves are converted using the translation amount and the rotation amount calculated in S500 and stored on the memory.

Concerning the displacement amount calculation in S700, the image reconstruction module 152 performs reconstruction based on ultrasound wave signals for one hundred data according to the coordinate position of the probe calculated in S600. The image reconstruction module 152 divides a reconstruction image into 2-mm square regions, calculates translation amounts and rotation amounts having a highest correlation respectively for the divided regions of the fiftieth image set in the ROI, and stores the translation amounts and the rotation amounts on the memory. ZNCC is used as a correlation index.

Concerning the projection position coordinate correction in S800, the image reconstruction module 152 performs fluctuation correction of projection position coordinate using the displacement amount in object stored on the memory in S700.

In S900, the image reconstruction module 152 reconstruction an image by applying a reconstruction algorithm by the UBP method for integrating the projection data in the ROI and weighting the projection data.

Figure 7:
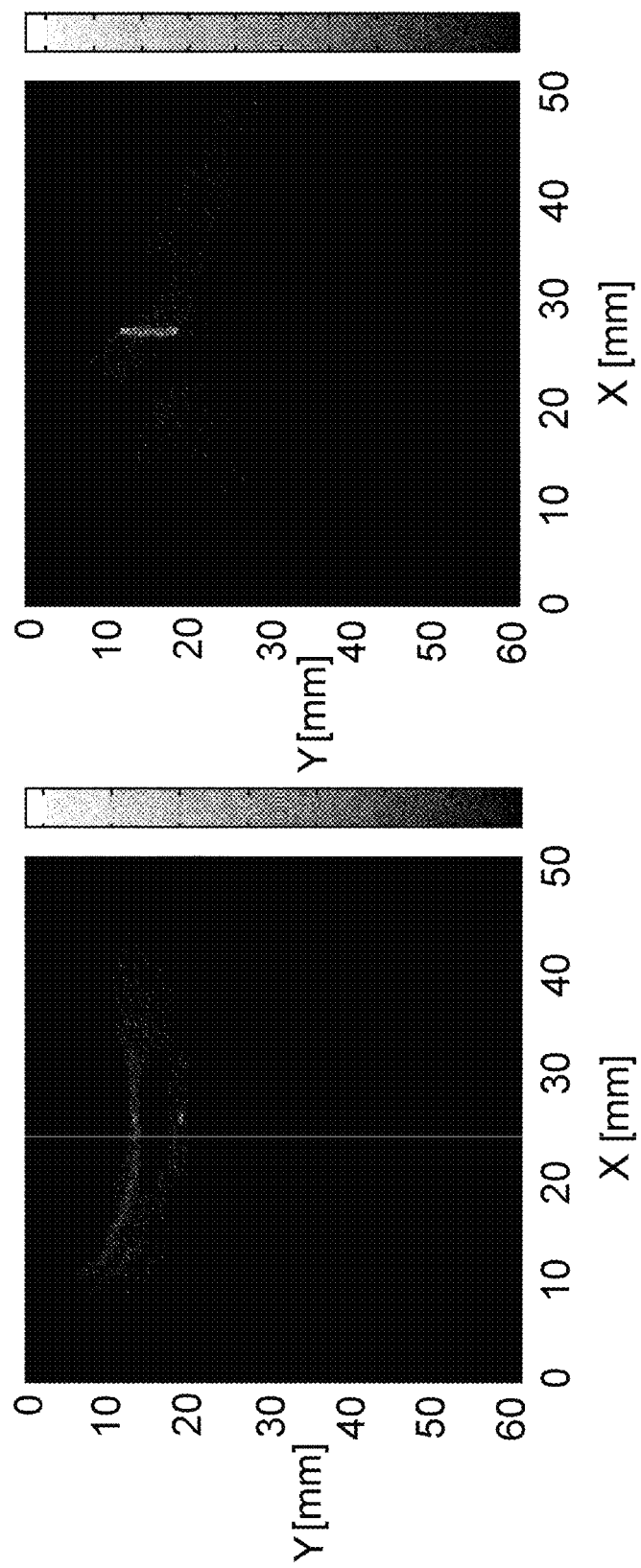
FIGS. 7A and 7B are diagrams showing a display screen of the object information acquiring apparatus according to the first embodiment.

An effect of visibility improvement by this method is shown in FIGS. 7A and 7B. In the figures, a columnar light absorber is reconstruction. In FIG. 7A, a reconstruction image by the conventional method is shown. On the other hand, in FIG. 7B, a reconstruction image by the method in this embodiment is shown. In general, observation of an acoustic wave from a light absorber arranged in the acoustic receiver in the vertical direction is difficult in principle. Therefore, in FIG. 7A, only upper and lower ends of the light absorber can be imaged. On the other hand, according to the method in this embodiment, since receiving positions of the photoacoustic wave (directions with respect to the object) vary, signals can be acquired from directions other than the vertical direction. Therefore, the columnar light absorber can be reproduced as shown in FIG. 7B.

The image in the conventional method and the image in the method of the present invention are compared with an actual arrangement shape of the light absorber. Then, whereas a reproduction degree in the conventional method is 3%, a reproduction degree in this method is nearly 100%. That is, it is seen that the shape of the light absorber can be more accurately reproduced by this method. This is because, by moving the probe and receiving the photoacoustic wave from more directions, an aperture of the probe is expanded and image data can be complemented. In this way, according to the present invention, even when there is limitation on the receiving direction of the probe, it is possible to acquire a reconstruction image with an artifact and noise reduced by moving the probe and substantially expanding the aperture. When the reconstruction image is acquired, appropriate processing such as coordinate system conversion is performed according to the position of the acoustic receiver. In this embodiment, since the correction is performed taking into account the displacement of the sound source inside the object due to the ultrasound wave image, it is possible to suppress the influence of movement of the acoustic receiver, a body motion, and the like and acquire a satisfactory image.

Second Embodiment

Figure 5:
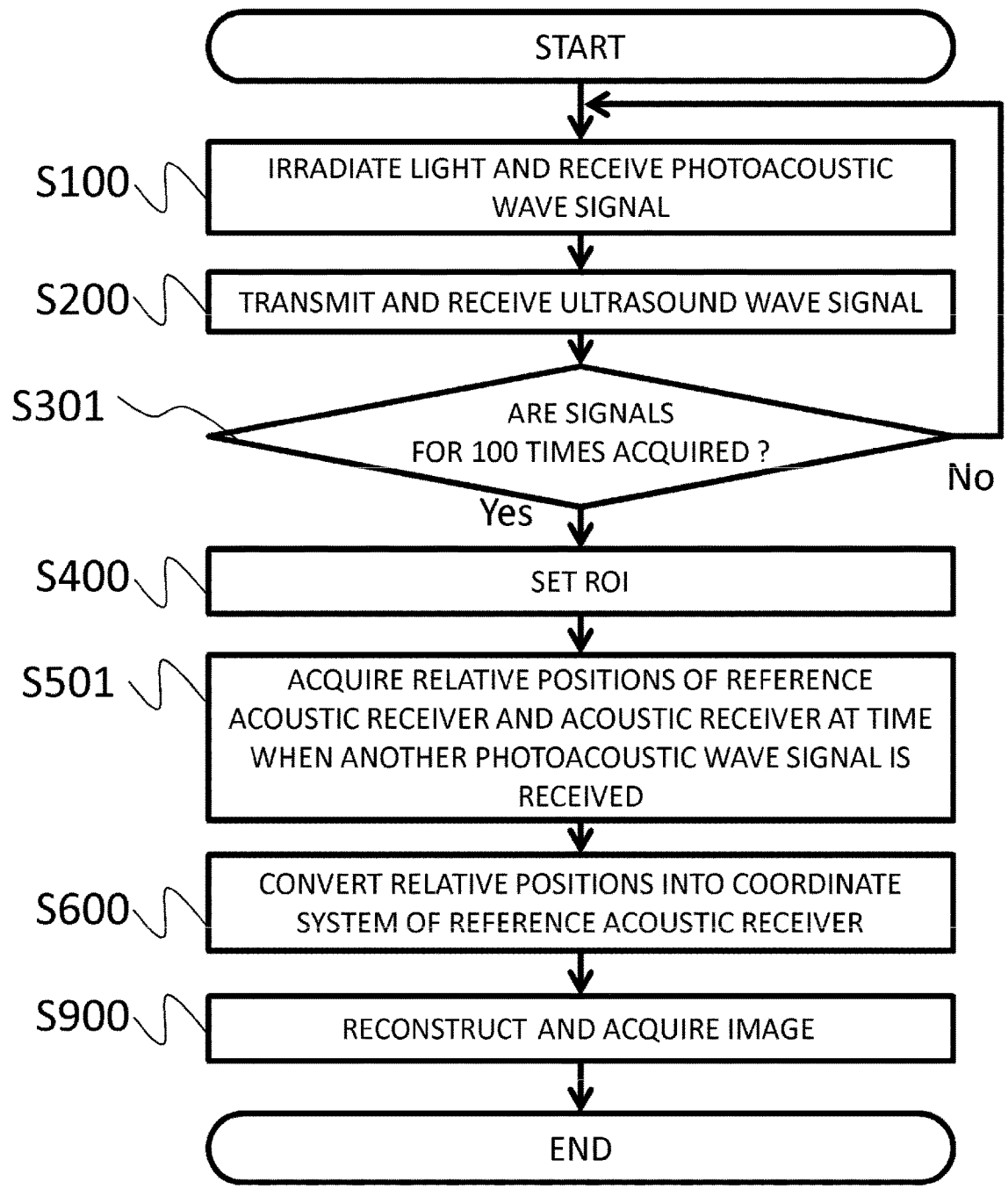
FIG. 5 is a diagram showing a processing flow of an object information acquiring apparatus according to a second embodiment.

In a second embodiment, a method of estimating a position of an acoustic receiver at the time of photoacoustic wave acquisition is explained. FIG. 5 is a processing flowchart of this embodiment. Explanation is omitted concerning portions common to the first embodiment.

The acoustic receiver 130 is a 1D linear array probe. The number of times of acquisition of signals is set to 100. Processing up to step S400 is the same as the processing in the first embodiment.

Subsequently, by the method shown in S501, a translation amount and a rotation amount are calculated as relative displacement with respect to the acoustic receiver in which the ROI is set on the basis of the ultrasound wave image. A translation amount and a rotation amount at a point equivalent to time when the photoacoustic wave is acquired are calculated by liner interpolation on the basis of the calculated values. A coordinate of the acoustic receiver at the time of the photoacoustic wave acquisition is estimated.

Subsequently, in S600, a coordinate system is converted using the translation amounts and the rotation amounts calculated in S501 and stored on the memory.

Then, in S900, on the basis of the coordinate system obtained in S600, an image is worked out by implementing reconstruction from 100 data.

Figure 8:
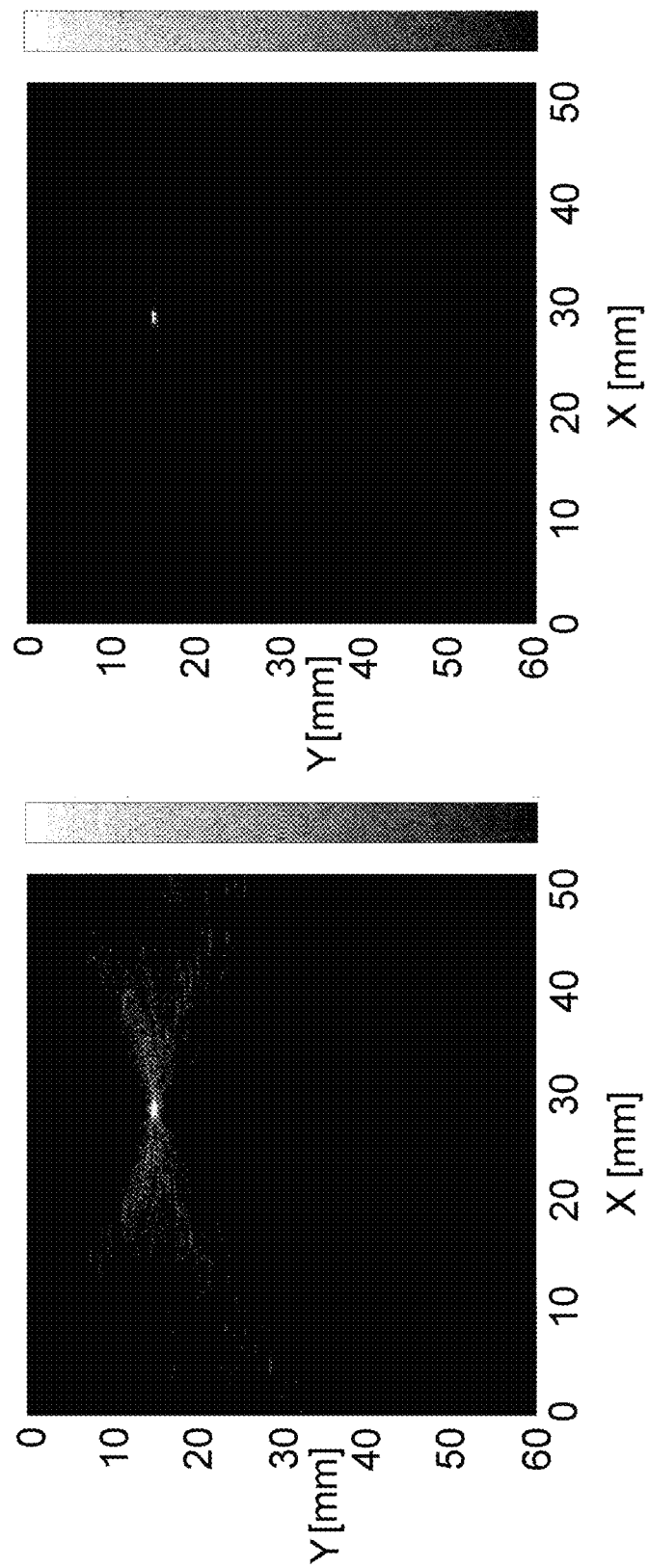
FIGS. 8A and 8B are diagrams showing a display screen of the object information acquiring apparatus according to the second embodiment.

An effect of visibility improvement by this method is shown in FIGS. 8A and 8B. In the figures, a dot-like light absorber having a diameter of 2 mm is reconstruction. In FIG. 8A, a reconstruction image by the conventional method is shown. On the other hand, in FIG. 8B, a result of image reconstruction by the method in this embodiment is shown. In FIG. 8A, since signal information for reconstruction an image is insufficient, reconstruction artifacts occur on the left and the right of a bright dot indicating the light absorber. On the other hand, in the method in this embodiment, since acquisition positions of the acoustic receiver (directions with respect to the object) vary, signals can be acquired from directions other than the vertical direction. As a result, as shown in FIG. 8B, the reconstruction artifacts can be suppressed and the shape of the light absorber can be reproduced.

The image in the conventional method and the image in the method of the present invention are compared with an actual arrangement shape of the light absorber. Then, whereas the size of the light absorber is 350% of an actual object in the conventional method as shown in FIG. 8A, the size of the light absorber is 110% in this method as shown in FIG. 8B. According to the method based on this embodiment, it is understood that the actual shape of the absorber can be reproduced accurately. That is, even if image data for reproducing an artifact in the conventional method is integrated, only the SN of the artifact increases. A shape different from a real shape is reproduced. On the other hand, according to this method, it is possible to suppress the artifact and reproduce the real shape.

Third Embodiment

Figure 11:
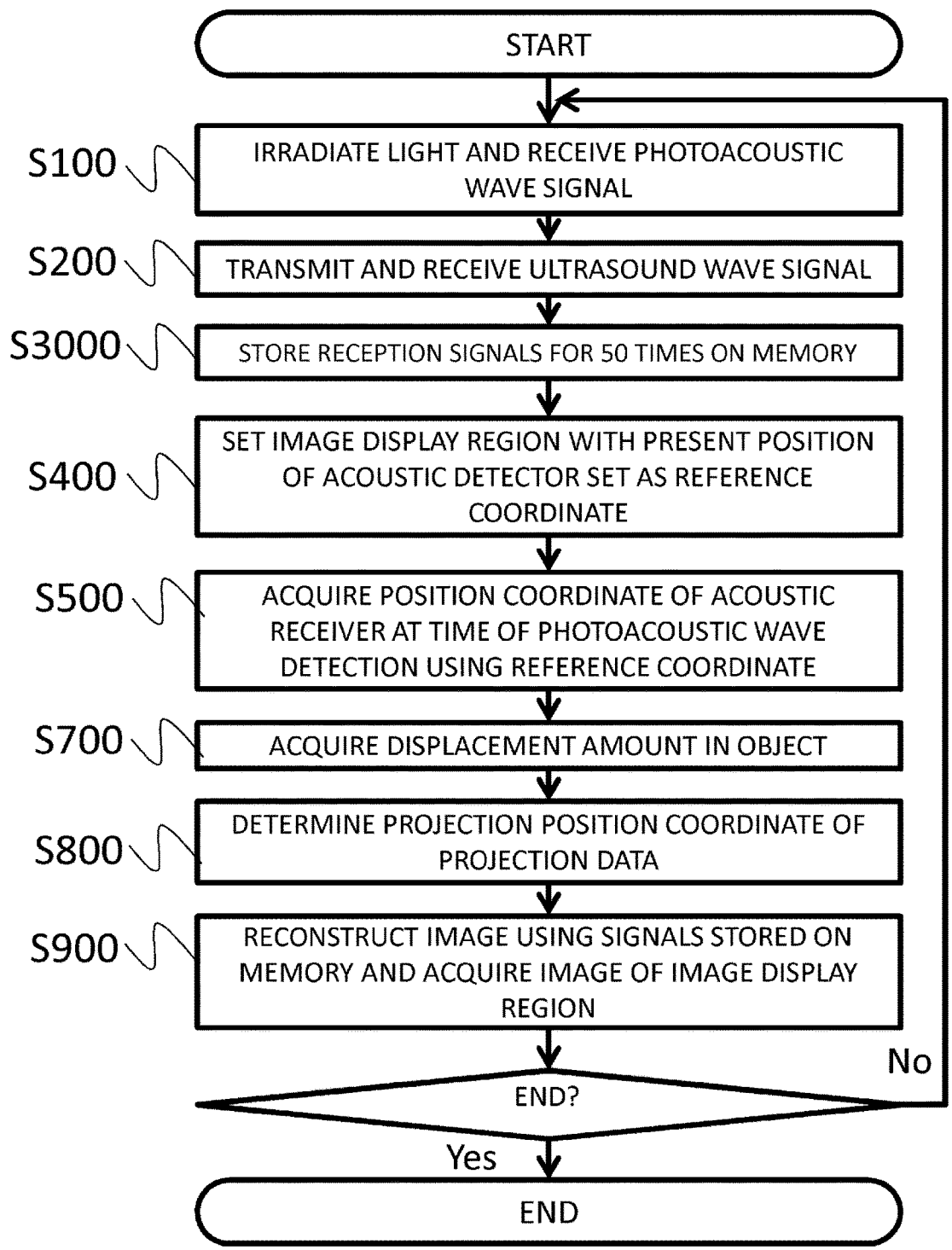
FIG. 11 is a diagram showing a processing flow of a test object information acquiring apparatus according to a third embodiment.

In this embodiment, a method of outputting an image on a real-time basis using data acquired in the past is explained with reference to a flow of FIG. 11.

An acoustic receiver is a 1D linear array probe. The number of times of acquisition of signals stored on the memory is set to 50.

First, in S100, light is irradiated on the object to acquire a photoacoustic wave signal.

Subsequently, in S200, an ultrasound wave is transmitted and received.

Subsequently, in S3000, signals acquired in S100 and S200 in maximum fifty times counted back from data acquired last are sequentially stored on the memory.

Subsequently, in S400, an image region obtained from an ultrasound wave acquired last is set as the ROI.

Subsequently, in S500, the position of the acoustic receiver at the time of the photoacoustic wave acquisition stored on the memory is calculated from an ultrasound wave image using the displacement amount calculation module 151.

Subsequently, in S700, displacement amount in object calculation is performed. In S800, correction of a projection position coordinate of projection data is performed using the displacement amount in object calculated in S700.

In S900, the image reconstruction module 152 reconstruction an image on the basis of a coordinate created in S500 by applying a reconstruction algorithm for superimposing projection data in the ROI created in S800.

When the process explained above is repeated an arbitrary number of times, by moving the position of the probe as appropriate, it is possible to virtually increase the number of probes and continue to display a reconstruction image while using past data on a real-time basis with data stored on the memory always continued to be updated. That is, according to this embodiment, it is possible to more accurately reproduce information concerning the inside of the object on a real-time basis.

Fourth Embodiment

Figure 6:
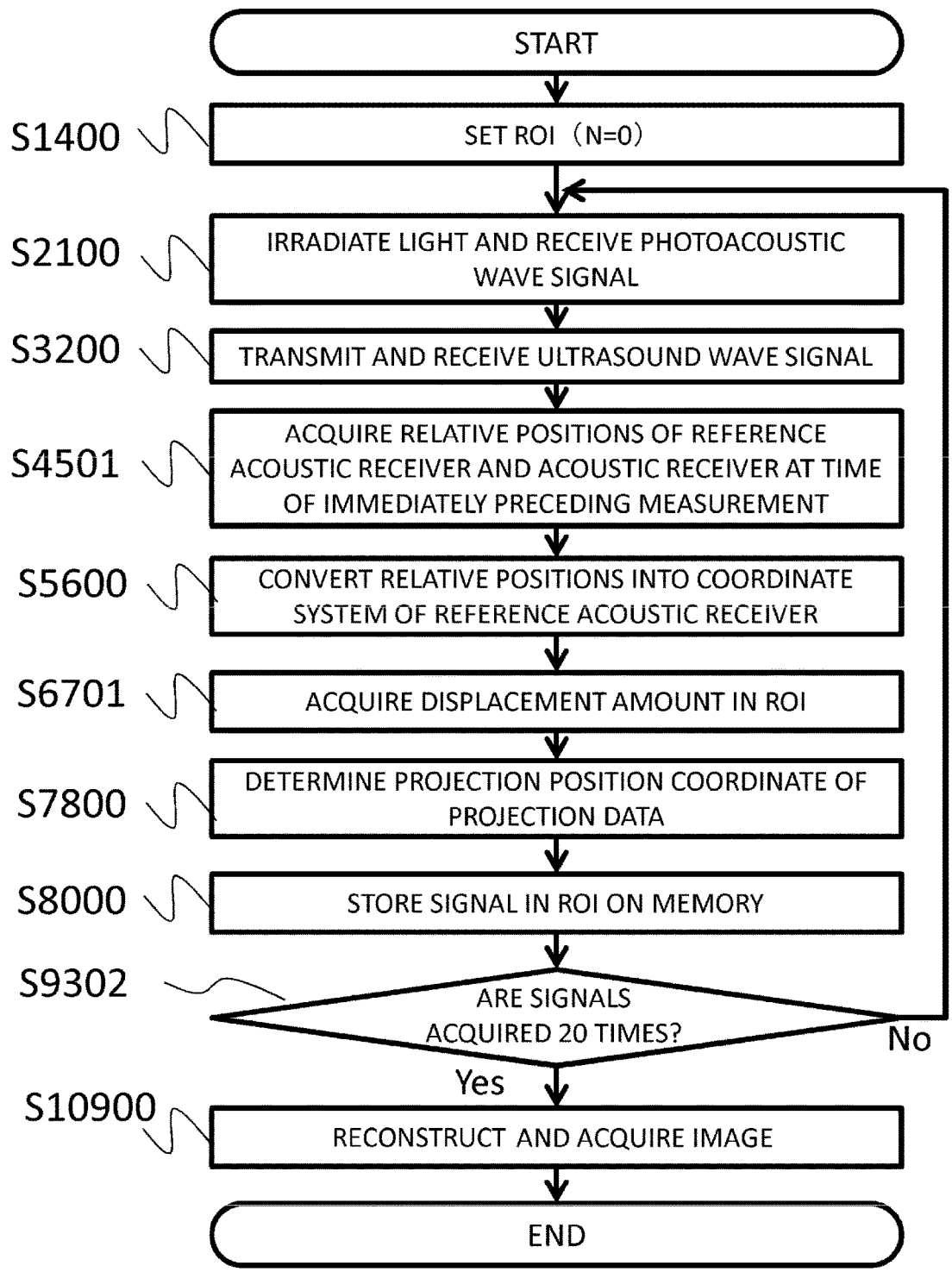
FIG. 6 is a diagram showing a processing flow of an object information acquiring apparatus according to a fourth embodiment.

In this embodiment, a method of performing calculation of a displacement amount of an acoustic receiver every time image data is acquired is explained with reference to a flow of FIG. 6. With this method, processing of calculation is distributed. An image can be output with a load on the memory suppressed.

The acoustic receiver 130 is a 1D linear array probe. The number of time of acquisition of signals is set to 100. A magnetic sensor is integrated with the acoustic receiver 130. The magnetic sensor detects a position and a tilting state of the acoustic receiver at the time of photoacoustic wave reception and transmits the position and the tilting state to the signal processing device 150.

First, in S1400, an image region obtained from an ultrasound wave for the first time is set as the ROI.

Subsequently, in S2100, light is irradiated on an object to acquire a photoacoustic wave signal.

Subsequently, in S3200, an ultrasound wave is transmitted and received.

Subsequently, in S4501, a translation amount and a rotation amount of the acoustic receiver from the position of the acoustic receiver at the time of the immediately preceding photoacoustic wave acquisition are calculated from an output value of the magnetic sensor with reference to the position of the acoustic receiver at the time of the ultrasound wave acquisition set in the ROI.

Subsequently, in S5600, a coordinate system is converted using the translation amount and the rotation amount calculated in S4501.

Subsequently, in S6701, image reconstruction of the ultrasound wave is performed to calculate an image on the basis of the coordinate system calculated in S5600. From a comparison result of the reconstruction image, a translation amount in the ROI (a movement amount in a direction (X) along the acoustic receiver and a movement amount in a lower surface direction (Y) perpendicular to the acoustic receiver) is calculated. That is, in S6701, the displacement amount in object is calculated.

Subsequently, in S7800, a projection position coordinate of projection data in the ROI of the photoacoustic wave is corrected on the basis of the value calculated in S6701.

Subsequently, in S8000, the corrected value in S7800 is stored on the memory.

The processing explained above is repeated twenty times according to S9302. A region stored on the memory at this point is shown in FIG. 9. A reconstruction region 910 is reconstruction from the acoustic receiver 920 directed to an obliquely upward direction in the figure. An imaged region 911 is reconstruction from the acoustic receiver 921 in a position after change. In this case, a region stored on the memory is a common image region 912.

Finally, in S10900, reconstruction is performed using data in a common portion for the twenty times.

With the method in this embodiment, it is possible to suppress use of the memory. Since a processing load is distributed, it is possible to improve processing speed and suitably carry out real-time processing. Since the acoustic receiver acquires signals from a plurality of directions, it is possible to suppress a reconstruction artifact that occurs when a place where a signal is not obtained is reconstruction. That is, according to this embodiment, it is possible to more accurately reproduce information in the object on a real-time basis.

Fifth Embodiment

Figure 12:
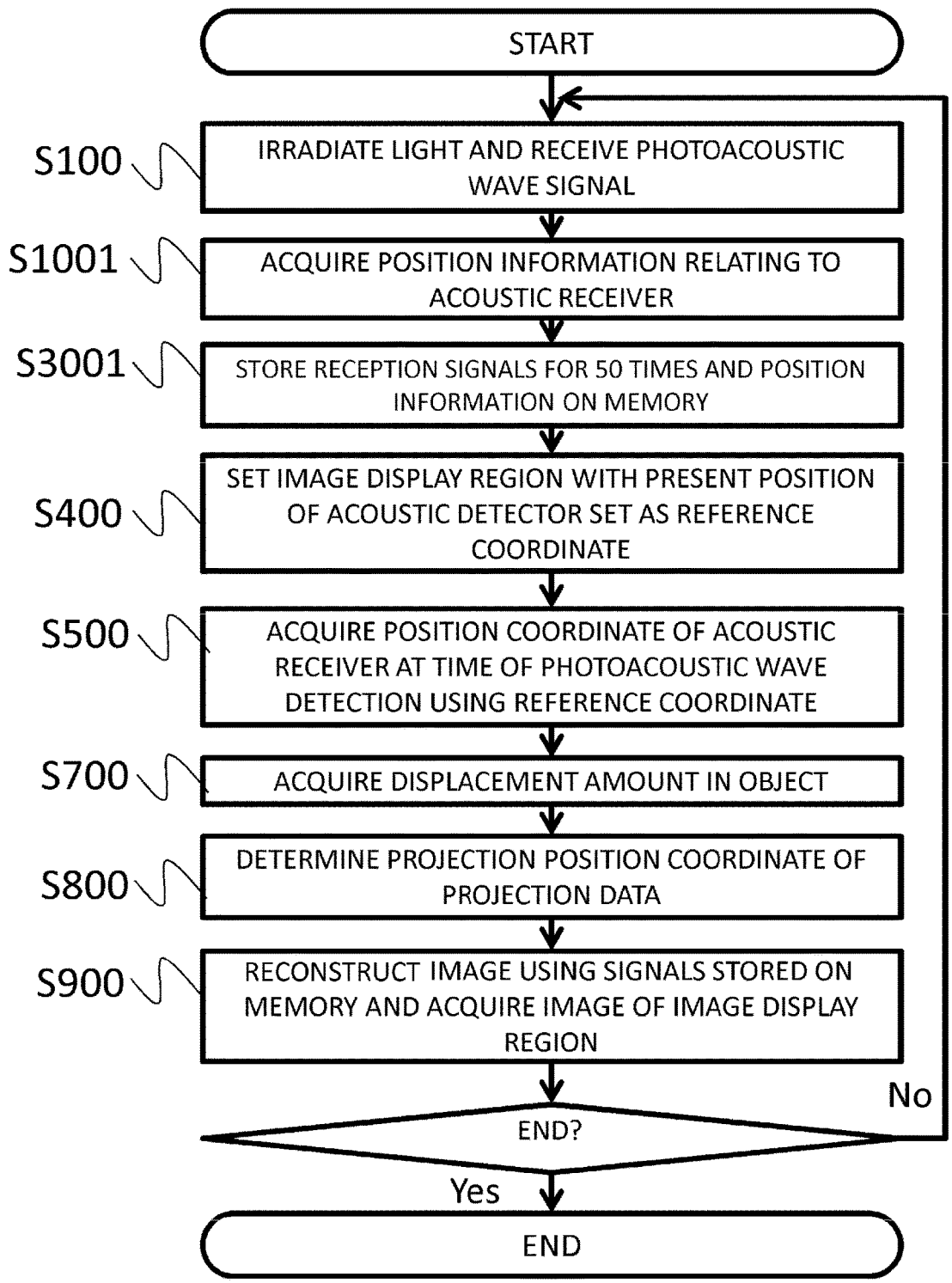
FIG. 12 is a diagram showing a processing flow of a test object information acquiring apparatus according to a fifth embodiment.

In this embodiment, a method of using, as an acoustic receiver, a probe in which transducers are three-dimensionally arranged is explained with reference to a flow of FIG. 12. With this method, it is possible to improve visibility using a three-dimensional reconstruction image.

Figure 13:
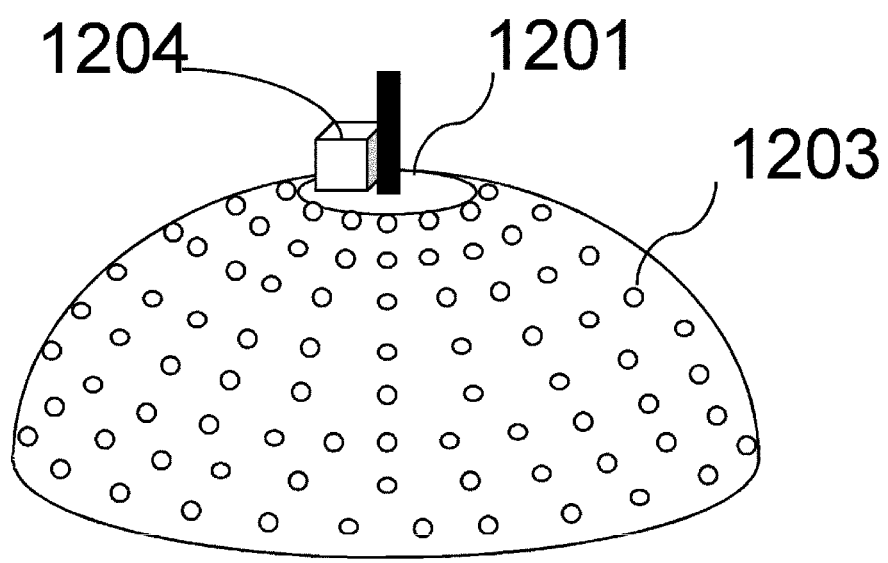
FIG. 13 is a diagram showing an acoustic receiver according to the fifth embodiment.

As the probe in which the transducers are three-dimensionally arranged, an acoustic receiver 1203 in which a large number of transducers are arranged on the surface of a hemisphere as shown in FIG. 13 is used. The inside of the hemisphere keeps acoustic coupling with a living body. A gel material that transmits light is encapsulated in the inside of the hemisphere. The lower surface of the hemisphere can be set on a plane. A light illuminating unit (1201) is provided in an upper surface section of the hemisphere. A magnetic sensor (1204) is integrally arranged in an adjacent section of the light illuminating unit. The magnetic sensor detects a position and a tilting state of the acoustic receiver at the time of photoacoustic wave reception and transmits the position and the tilting state to the signal processing device 150.

The number of times of acquisition of signals stored on the memory is set to 50.

First, in S100, light is irradiated on an object to acquire a photoacoustic wave signal.

Subsequently, in S1001, data of the magnetic sensor at a point when S100 is carried out is received.

Subsequently, in S3001, the signals acquired in S100 and S1001 for maximum fifty times counted back from data acquired last are sequentially stored on the memory.

Subsequently, in S400, a volume region having a volume of 2 cm$^3$ right under the probe at a point of last acquisition is set as the ROI.

Subsequently, in S500, a three-dimensional position coordinate of the acoustic receiver at the time of the photoacoustic wave reception stored on the memory is calculated from the magnetic sensor data stored on the memory with reference to a position coordinate of the acoustic receiver at the point of the last acquisition.

Subsequently, in S700, displacement amount in the object calculation is performed. In S800, correction of a projection position coordinate of projection data is performed using the displacement amount in the object calculated in S700.

In S900, the image reconstruction module 152 creates projection data on the basis of the three-dimensional position coordinate created in S500 and the reception signals stored on the memory. The image reconstruction module 152 reconstruction an image by applying a reconstruction algorithm for three dimensionally superimposing the projection data in the ROI.

When the process explained above is repeated an arbitrary number of times, by moving the position of the acoustic receiver as appropriate, it is possible to virtually increase the number of acoustic receivers and continue to display a three-dimensional reconstruction image while using past data on a real-time basis with data stored on the memory always continued to be updated. That is, according to this embodiment, it is possible to more accurately three-dimensionally reproduce information concerning the inside of the object on a real-time basis.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-088195, filed on Apr. 19, 2013, which is hereby incorporated by reference herein its entirety.

What is claimed is:

1. An apparatus comprising:
a light source;
a receiver configured to receive a photoacoustic wave generated from an object by irradiation of the object with light emitted from the light source;
a memory; and
a processor configured to acquire image data,
wherein the light source is configured to emit light at a plurality of timings,
the receiver is configured to output a plurality of signals corresponding to the plurality of timings by receiving the photoacoustic wave generated at the plurality of timings,
the memory is configured to store the plurality of signals, and
the processor is configured to:
acquire a plurality of photoacoustic image data corresponding to the plurality of timings by using the plurality of signals read out from the memory,
determine, by using the plurality of photoacoustic image data, a plurality of projection positions corresponding to the plurality of timings, and
reconstruct and acquire a photoacoustic image, based on an angle between the receiver and the plurality of projection positions, using the plurality of signals read out from the memory and the following:

$$p_0(r) = \int_{\Omega_0} b(r_0, t = |r - r_0|) \frac{d\Omega_0}{\Omega_0} \qquad (7)$$

and $$d\Omega_0 = \frac{dS_0}{|r - r_0|^2} \cos\theta, \qquad (9)$$

where $p_0(r)$ is an initial sound pressure distribution, $r_0$ is a position of the receiver, r is a projection position, t is a time, θ is the angle between the receiver and a projection position, $dS_0$ is an area of a reception surface of the receiver, and $b(r_0, t)$ is a projection data term extracted using t with respect to a projection position according to one of the following:

$$b(r_0, t) = p(r_0, t) - 2t \frac{\partial p(r_0, t)}{\partial t} \qquad (8)$$

or $$b(r_0, t) = -2t \frac{\partial p(r_0, t)}{\partial t}. \qquad (10)$$

2. The apparatus according to claim 1, further comprising a display unit configured to display an image on the basis of the photoacoustic image data.

3. The apparatus according to claim 1, wherein the receiver is configured to change a relative position of the receiver and the object.

4. An apparatus comprising:
a light source;
a receiver configured to receive a photoacoustic wave generated from an object by irradiation of the object with light emitted from the light source;
a probe configured to transmit ultrasound to the object and output a second signal by receiving an echo wave generated from the object by reflection of the ultrasound;
a memory; and
a processor configured to acquire image data,
wherein the light source is configured to emit light at a plurality of timings,
the receiver is configured to output a first plurality of signals corresponding to the plurality of timings by receiving the photoacoustic wave generated at the plurality of timings,
the probe is configured to output, by transmitting and receiving the ultrasound to and from the object in an interval of the plurality of timings, a second plurality of signals,
the memory is configured to store the first plurality of signals and the second plurality of signals, and
the processor is configured to:
acquire, by using the second plurality of signals read out from the memory, a plurality of ultrasound image data,
determine, by using the plurality of ultrasound image data, a plurality of projection positions corresponding to the plurality of timings, and
reconstruct and acquire a photoacoustic image, based on an angle between the receiver and the plurality of projection positions, using the first plurality of signals read out from the memory and the following:

$$p_0(r) = \int_{\Omega_0} b(r_0, t = |r - r_0|) \frac{d\Omega_0}{\Omega_0} \quad (7)$$

and $$d\Omega_0 = \frac{dS_0}{|r - r_0|^2} \cos\theta, \quad (9)$$

where $p_0(r)$ is an initial sound pressure distribution, $r_0$ is a position of the receiver, $r$ is a projection position, $t$ is a time, $\theta$ is the angle between the receiver and a projection position, $dS_0$ is an area of a reception surface of the receiver, and $b(r_0, t)$ is a projection data term extracted using $t$ with respect to a projection position according to one of the following:

$$b(r_0, t) = p(r_0, t) - 2t \frac{\partial p(r_0, t)}{\partial t} \quad (8)$$

or $$b(r_0, t) = -2t \frac{\partial p(r_0, t)}{\partial t}. \quad (10)$$

5. An apparatus comprising:
a light source;
a receiver including transducers configured to output a signal by receiving a photoacoustic wave generated from an object by irradiation of light emitted from the light source;
a memory; and
a processor configured to acquire image data,
wherein the light source is configured to emit light at a plurality of timings,
the receiver is configured to output a plurality of signals corresponding to the plurality of timings by receiving the photoacoustic wave generated at the plurality of timings,
the memory is configured to store the plurality of signals, and
the processor is configured to:
acquire information on a position and a tilting state of the receiver corresponding to the plurality of timings,
determine, based on the information on the position and the tilting state of the receiver corresponding to the plurality of timings, a plurality of projection positions corresponding to the plurality of timings, and
reconstruct and acquire a photoacoustic image, based on an angle between the receiver and the plurality of projection positions, using the plurality of signals read out from the memory and the following:

$$p_0(r) = \int_{\Omega_0} b(r_0, t = |r - r_0|) \frac{d\Omega_0}{\Omega_0} \quad (7)$$

and $$d\Omega_0 = \frac{dS_0}{|r - r_0|^2} \cos\theta, \quad (9)$$

where $p_0(r)$ is an initial sound pressure distribution, $r_0$ is a position of the receiver, $r$ is a projection position, $t$ is a time, $\theta$ is the angle between the receiver and a projection position, $dS_0$ is an area of a reception surface of the receiver, and $b(r_0, t)$ is a projection data term extracted using $t$ with respect to a projection position according to one of the following:

$$b(r_0, t) = p(r_0, t) - 2t \frac{\partial p(r_0, t)}{\partial t} \quad (8)$$

or $$b(r_0, t) = -2t \frac{\partial p(r_0, t)}{\partial t}. \quad (10)$$

6. The apparatus according to claim 1, wherein the receiver includes transducers that are arranged three-dimensionally.

7. The apparatus according to claim 6, wherein the transducers are arranged on a surface of a hemisphere.

8. The apparatus according to claim 7, wherein the receiver is a handheld probe.

9. The apparatus according to claim 4, wherein the receiver has a function of the probe.

10. The apparatus according to claim 9, wherein the receiver includes transducers that are arranged on a surface of a hemisphere.

11. The apparatus according to claim 10, wherein the receiver is a handheld probe.

12. The apparatus according to claim 4, wherein the processor is configured to determine the plurality of projection positions according to a speckle tracking method using the plurality of ultrasound image data.

13. The apparatus according to claim 4, wherein the processor is configured to acquire information on a position and a tilting state of the receiver by applying a block matching method to the plurality of ultrasound image data.

14. The apparatus according to claim 5, wherein the receiver includes a sensor configured to detect the position and the tilting state of the receiver, and wherein the processor is configured to acquire the information on the position and the tilting state of the receiver detected by the sensor.

15. The apparatus according to claim 14, wherein the sensor is a magnetic sensor or an optical sensor.

* * * * *